United States Patent
Alsop et al.

(10) Patent No.: US 10,302,722 B2
(45) Date of Patent: May 28, 2019

(54) SYSTEM AND METHOD FOR MAGNETIC RESONANCE IMAGING USING EXCHANGE TIME REFLECTIVE OF MOTION RESTRICTION OR SPIN DIFFUSION OF PROTONS BOUND TO MACROMOLECULES

(71) Applicants: David Alsop, Newton, MA (US); Gopal Varma, Boston, MA (US)

(72) Inventors: David Alsop, Newton, MA (US); Gopal Varma, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 744 days.

(21) Appl. No.: 14/776,872

(22) PCT Filed: Mar. 13, 2014

(86) PCT No.: PCT/US2014/026077
§ 371 (c)(1),
(2) Date: Sep. 15, 2015

(87) PCT Pub. No.: WO2014/151596
PCT Pub. Date: Sep. 25, 2014

(65) Prior Publication Data
US 2016/0041246 A1 Feb. 11, 2016

Related U.S. Application Data

(60) Provisional application No. 61/791,655, filed on Mar. 15, 2013, provisional application No. 61/791,793, filed on Mar. 15, 2013.

(51) Int. Cl.
*G01R 33/56* (2006.01)
*G01R 33/48* (2006.01)
(Continued)

(52) U.S. Cl.
CPC .......... *G01R 33/5605* (2013.01); *A61B 5/055* (2013.01); *A61B 5/4041* (2013.01);
(Continued)

(58) Field of Classification Search
CPC ..... A61B 5/055; A61B 5/4041; A61B 5/7278; G01R 33/4828; G01R 33/50; G01R 33/5605; G01R 33/5659
See application file for complete search history.

(56) References Cited

U.S. PATENT DOCUMENTS

| 5,429,134 | A | 7/1995 | Foo | |
|---|---|---|---|---|
| 6,968,225 | B2 | 11/2005 | Vu | |
| 2011/0241669 | A1* | 10/2011 | Chen | G01R 33/5611 324/309 |

FOREIGN PATENT DOCUMENTS

| WO | 2009060403 | 5/2009 |
|---|---|---|
| WO | 2011091365 | 7/2011 |

OTHER PUBLICATIONS

International Search Report and Written Opinion dated Sep. 12, 2014 for International Application No. PCT/US2014/026077.
(Continued)

*Primary Examiner* — Jay Patidar
(74) *Attorney, Agent, or Firm* — Quarles & Brady LLP

(57) ABSTRACT

A system and method for producing a report about a subject from data collected from the subject using a magnetic resonance imaging (MRI) system. The method includes directing the MRI system to perform a pulse sequence to manipulate exchangeable magnetization in the subject and acquiring, with the MRI system, imaging data from the subject in response to the pulse sequence. The method also includes analyzing the effects of the frequencies of applied RF energy on the imaging data to identify inhomogeneous lines formed by a summation of multiple sublines centered at multiple different frequencies. The method further
(Continued)

includes generating a report pertaining to inhomogeneous magnetization transfer occurring in the subject in response to the pulse sequence.

18 Claims, 4 Drawing Sheets

(51) Int. Cl.
    *A61B 5/055*     (2006.01)
    *A61B 5/00*     (2006.01)
    *G01R 33/565*     (2006.01)
    *G01R 33/50*     (2006.01)

(52) U.S. Cl.
    CPC ........ *A61B 5/7278* (2013.01); *G01R 33/4828* (2013.01); *G01R 33/50* (2013.01); *G01R 33/5659* (2013.01)

(56) References Cited

OTHER PUBLICATIONS

Balezeau et al, Mapping of Low Flip Angles in Magnetic Resonance, Physics in Medicine and Biology 56(20) Sep. 23, 2011, entire document.

Alsop, et al., Inhomogeneous Magnetization Transfer Imaging of Myelin Concentration in Multiple Sclerosis, Proc. Intl. Soc. Mag. Reson. Med., 2007, 15:2188.

Chan, et al., Nuclear Relaxation Studies of Lecithin Bilayers, Nature, 1971, 231:110-112.

Feigenson, et al., Nuclear Magnetic Relaxation Behavior of Lecithin Multilayers, Journal of the American Chemical Society, 1974, 96(5):1312-1319.

Helms, et al., High-Resolution Maps of Magnetization Transfer with Inherent Correction for RF Inhomogeneity and T1 Relaxation Obtained from 3D Flash MRI, Magnetic Resonance in Medicine, 2008, 60:1396-1407.

Henkelman, et al., Quantitative Interpretation of Magnetization Transfer, Magnetic Resonance in Medicine, 1993, 29 (6):759-766.

Manning, et al., The Physical Mechanism of "Inhomogeneous" Magnetization Transfer MRI, Journal of Magnetic Resonance, 2017, 274:125-136.

Seiter, et al., Molecular Motion in Lipid Bilayers. A Nuclear Magnetic Resonance Line Width Study, Journal of the American Chemical Society, 1973, 95(23):7541-7553.

Varma, et al., Quantitative Evaluation of the Exchange Time and T2 Associated with an Inhomogeneous Component Using Inhomogeneous Magnetization Transfer Imaging, Proc. Intl. Soc. Mag. Reson. Med., 2013, 21:2536.

Varma, et al., Extracting a Robust Inhomogeneous Magnetization Transfer (ihMT) Rate Parameter, ihMt-R, Proc. Intl. Soc. Mag. Reson. Med., 2015, 23:3357.

Varma, et al., Interpretation of Magnetization Transfer from Inhomogeneously Broadened Lines (ihMT) in Tissues as a Dipolar Order Effect Within Motion Restricted Molecules, Journal of Magnetic Resonance, 2015, 260:67-76.

Varma, et al., In Vivo Measurement of a New Source of Contrast, the Dipolar Relaxation Time, T1D, Using a Modified Inhomogeneous Magnetization Transfer (ihMT) Sequence, Magnetic Resonance in Medicine, 2017, 78:1362-1372.

Ward, et al., A New Class of Contrast Agents for MRI Based on Proton Chemical Exchange Dependent Saturation Transfer (CEST), Journal of Magnetic Resonance, 2000, 143(1):79-87.

European Patent Office, Extended European Search Report, Application No. 14770586.7, dated Nov. 16, 2017, 14 pages.

\* cited by examiner

SYSTEM AND METHOD FOR MAGNETIC RESONANCE IMAGING USING EXCHANGE TIME REFLECTIVE OF MOTION RESTRICTION OR SPIN DIFFUSION OF PROTONS BOUND TO MACROMOLECULES

CROSS-REFERENCE TO RELATED APPLICATIONS

This application represents the U.S. National Stage of International Application No. PCT/US2014/026077, filed Mar. 13, 2014 which is based on, claims priority to, and incorporates herein by reference in their entirety, U.S. Provisional Application Ser. No. 61/791,655, filed Mar. 15, 2013, and entitled, "SYSTEM AND METHOD FOR PRODUCING A BIOMARKER USING INHOMOGENEOUS MAGNETIZATION TRANSFER MAGNETIC RESONANCE IMAGING" and U.S. Provisional Application Ser. No. 61/791,793, filed Mar. 15, 2013, and entitled "SYSTEM AND METHOD FOR INHOMOGENEOUS MAGNETIZATION TRANSFER MAGNETIC RESONANCE IMAGING."

STATEMENT REGARDING FEDERALLY SPONSORED RESEARCH

This invention was made with government support under NS047029 awarded by the National Institutes of Health and W81XWH-10-1-0713 awarded by the Department of Defense. The government has certain rights in the invention.

BACKGROUND OF THE INVENTION

The field of the invention is systems and methods for magnetic resonance imaging ("MRI"). More particularly, the invention relates to systems and methods for measurement of inhomogeneous magnetization transfer ("IHMT") using MR techniques. These methods show high specificity for certain tissues and samples, such as myelin.

MRI can be used to measure the exchange of magnetization between molecules, and can thus provide unique information about the chemical and molecular environment of samples or tissues. One type of such exchange measurement is broadly referred to in the field as magnetization transfer ("MT"). This technique is capable of measuring the exchange of magnetization from spin species, such as the nuclei of hydrogen atoms (often referred to by the synonym protons), whose motion is restricted because they are bound to macromolecules. These so-called "bound pool" spin species have very short transverse relaxation times ("$T_2$") as a result of being tightly bound to their environment. For example, $T_2$ can be as short as 10-50 µs for some bound pool spin species. As a result, these bound pool spins are difficult to image with traditional methods. The magnetization of bound pool spins, however, can exchange rapidly with so-called "free pool" spins that are not tightly bound to their environment. Such "free pools" exist (or are present) as, for example, water protons in many soft tissue environments.

The properties of the bound pool can thus be probed by applying RF power at a frequency offset from water. This applied power has little direct effect on the free pool, but will tend to directly saturate the bound pool. The saturated bound pool magnetization then exchanges with the free pool to thereby decrease the measurable magnetic resonance signal.

Despite extensive studies, magnetization transfer has not yielded widely recognized diagnostic benefits. As an example, for approximately a decade, there was significant interest in the use of MT for different clinical applications. One such application was the characterization of myelination as it relates to multiple sclerosis. It gradually became appreciated, however, that MT offered little specificity to imaging myelin, and that MT contrast generally was typically closely related to $T_1$ and $T_2$ contrasts. Although there are some signs of special sensitivity, they have generally been overwhelmed by the low contrast between myelinated and unmyelinated tissues and by the sensitivity of the MT technique to scanning imperfections. As an example of the low MT contrast between myelin and other tissue types, traditional MT shows as much or more signal in muscle and skin than in myelinated tissues.

It would therefore be desirable to provide a system and method for magnetization transfer MRI techniques that are more diverse and/or can elicit additional contrast mechanisms.

SUMMARY OF THE INVENTION

The present invention overcomes the aforementioned drawbacks by providing systems and methods for imaging using inhomogeneous magnetization transfer ("IHMT") magnetic resonance imaging ("MRI") techniques. In some configurations, multiple images may be acquired and selectively combined to produce images using the IHMT contrast mechanism. For example, multiple images, such as three images, are acquired. One image may be acquired with radio frequency ("RF") saturation energy applied at a first frequency and another image may be acquired with RF saturation energy applied at a second frequency that is different from the first. Still another image may be acquired with RF saturation energy applied at a both the first and second frequencies. Through a selective combination of the images, a new and unexpected form of clinically-useful images can be obtained.

It is an aspect of the invention to provide a method for producing a report about a subject from data collected from the subject using a magnetic resonance imaging (MRI) system. The method includes directing the MRI system to perform a pulse sequence to manipulate exchangeable magnetization of bound pool protons in the subject and acquiring, with the MRI system, imaging data from the subject in response to the pulse sequence. The method also includes analyzing effects of the frequencies of applied RF energy on the imaging data to identify inhomogeneous lines formed by a summation of multiple sublines centered at multiple different frequencies. The method further includes generating a report pertaining to inhomogeneous magnetization transfer occurring in the subject in response to the pulse sequence based on the inhomogeneous lines.

In another aspect of the invention, a method is provided for determining at least one of an exchange rate and a density, or concentration, of protons contributing to the inhomogeneous magnetization transfer line using the foregoing method. For example, to perform the method, a pulse sequence designed to apply radio frequency (RF) energy is repeated a plurality of times and, during each repetition, at least one of a power and a pulsing rate of the RF energy is changed while maintaining consistent first and second frequencies. In this manner, a plurality of images are produced. These images are indicative of at least one of an exchange rate and density, or concentration, of protons contributing to the inhomogeneous magnetization transfer line.

In accordance with another aspect of the invention, a magnetic resonance imaging (MRI) system is disclosed that includes a magnet system configured to generate a polarizing magnetic field about at least a region of interest (ROI) of a subject arranged in the MRI system, a plurality of gradient coils configured to apply a gradient field with respect to the polarizing magnetic field, and a radio frequency (RF) system configured to apply RF excitation fields to the subject and acquire MR image data therefrom. The system also includes a computer programmed to control the plurality of gradient coils and RF system to perform at least one pulse sequence that includes applying RF energy at least at two frequencies to manipulate exchangeable magnetization from protons in the subject. The computer is further programmed to control the plurality of gradient coils and RF system to acquire imaging data including magnetization transfer information from the exchangeable magnetization from protons in the subject in response to the pulse sequence. The computer is also programmed to generate a report pertaining to inhomogeneous magnetization transfer occurring in the subject in response to the pulse sequence by analyzing the effects of the frequencies of applied RF energy on the imaging data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
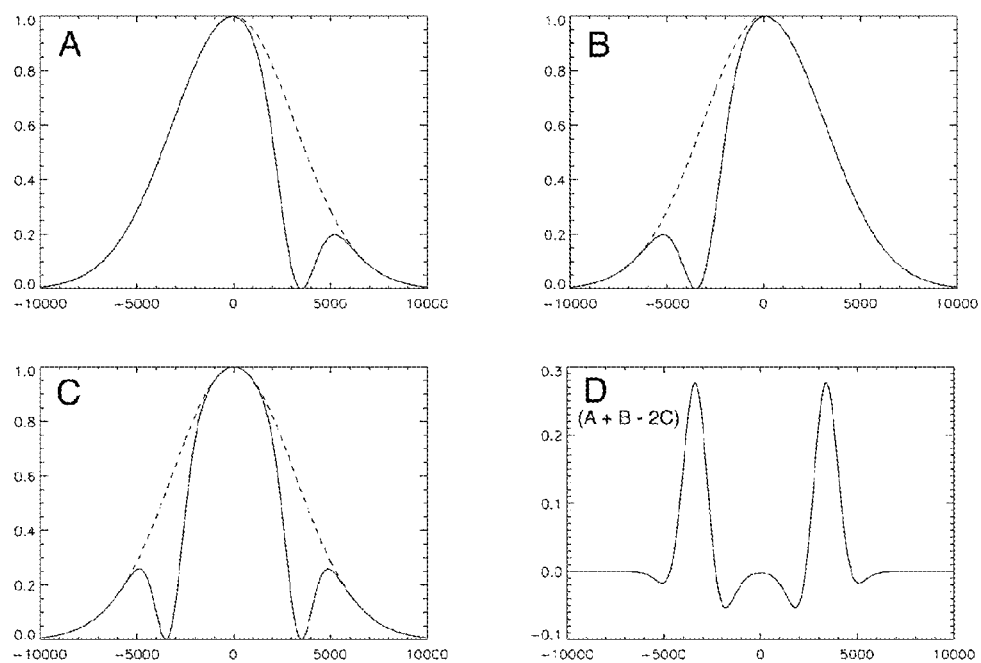
FIGS. 1A-1D is a set of graphs illustrating, in FIGS. 1A-1C that varied information can be acquired using an imaging technique in accordance with the present invention and be combined, in FIG. 1D, to derive inhomogeneous magnetization transfer information.

Described herein is a system and method for inhomogeneous magnetization transfer ("IHMT") magnetic resonance imaging ("MRI") that is capable of providing new and different contrast for MR imaging. As a non-limiting example, this contrast mechanism can be used to elicit information specific to myelin and its functional equivalents. For example, as discussed below, the present invention is capable of imaging magnetization transfer from methylene ($-CH_2-$) chains in lipid bilayers in myelin to a free pool of water protons. It will thus be appreciated by those skilled in the art that the present invention is applicable not only to myelin, but for other molecular targets that include lipid bilayers or other functionally equivalent groups having exchangeable magnetization of protons.

The spin state of exchangeable magnetization of bound pool protons, such as methylene ($-CH_2-$) chains in the lipid bilayer of myelin, can be utilized to influence the spin state of water protons through magnetization exchange processes. As such, it is noted that this exchange does not refer to protons that exchange themselves; rather, in the context of the present invention, "exchange" refers to the exchange of magnetization of the protons, rather than the protons themselves. That is, the magnetization of the protons is exchanged through spin diffusion and other processes. Thus, in the context of the present invention, protons that contribute to the inhomogeneous component of magnetization transfer, for example, because of their restricted motion and slow spin diffusion, are also referred to as IHMT protons or IHMT contributing protons.

The exchangeable magnetization of bound pool protons can be saturated by applying RF energy thereto. The saturation of these protons is subsequently transferred to the free water protons, depending upon the rate of exchange between the two spin populations, and hence is detectable with MRI. It is the transfer of this saturation through the exchange of magnetization between certain bound pool and free water protons that forms the basis of imaging the contrast mechanisms used in the following IHMT methods.

A short T2, which indicates a short transverse magnetization recovery, results in spins quickly becoming out of phase and experiencing different resonance conditions. From a frequency perspective, this dephasing results in broad frequency peaks or "broad lines". A short T2 or broad line from bound spins reflects the magnetic interactions between different protons, which are referred to dipolar coupling. The reason free water does not exhibit such a broad line is that all the protons in water are moving so quickly relative to each other that the positive and negative interactions quickly average away. In large molecules, however, motion is restricted and averaging is not effective. Therefore, in large molecules, some protons experience a positive coupling with nearby protons and others experience a negative. Still, over some time period, this coupling typically does change.

The present disclosure recognizes that, in most large molecules like proteins, small motions of the nuclei and the coupling across large numbers of protons cause an effect known as spin diffusion that causes gradual modulation of the positive and negative couplings. For smaller molecules, rotation will also fairly rapidly average the positive and negative effects. As a result, power applied at one frequency does not just affect certain protons but instead the saturation is spread by spin diffusion and rotation across all frequencies. This response of the "whole line" as one is known as "homogenous broadening." Homogenous broadening is generally assumed for in-vivo magnetization transfer. However, situations without this spread of saturation across frequencies may occur in some chemical structures, typically in small systems of just a few protons that are rotationally restricted. Such broadening without mixing across frequencies is known as inhomogeneous broadening. When analyzing frequency information, this results in an inhomogeneous line that is composed or formed of sublines that are associated with the protons that are rotationally restricted.

A general feature of homogenously broadened lines is that RF power applied at one frequency will have a similar effect to power applied at a different frequency as long as the amplitude is adjusted to achieve similar saturation. The MT effect at positive and negative frequency is virtually identical; hence, applying power split between positive and negative frequency can provide the same saturation as applying the full power at one frequency.

Over time, small errors have been observed in the performance of various imaging techniques that were, without a full understanding of the underlying phenomenon, attributed to MT effects. For example, even in some perfusion imaging techniques, such residual errors were noticed. With careful analysis and research and targeted experiments in accordance with the present disclosure, such phenomenon were probed.

In one such endeavor, a three fold subtraction using three different images is performed. Alternating positive and negative frequency pulses of irradiation may be applied. The frequency for positive and negative pulses may be within the width of the inhomogeneous line from methylene (—CH$_2$—) chains, such as in lipid bilayers in myelin.

Referring now to FIG. 1, a set of diagrams illustrating the basic concept of IHMT are provided. As shown in FIG. 1, three imaging data sets (A-C) are obtained. Imaging data set A is obtained under a positive frequency irradiation. Imaging data set B is obtained under a negative frequency irradiation having the same power as that of imaging data set A otherwise. Imaging data set C is obtained under a dual frequency irradiation having both a negative and a positive frequency irradiation and each of the negative and the positive frequency has one half of the power of that used in imaging data sets A or B. As the magnetization at a particular frequency is saturated by one radio frequency (RF) having certain power, it will still be mostly saturated by the same RF having half of the certain power. The resulting imaging date set C shows more attenuation of the line following dual frequency irradiation. Imaging data set D shows an IHMT image after subtracting two times the dual frequency image (imaging data set C) from the sum of the positive (imaging data set A) and negative (imaging data set B) images. In this example, only the inhomogeneous broadening remained, while the homogeneous broadening canceled. Mathematically, this can be represented as:

$$IHMT_1 = A + B - 2C \quad (1).$$

As another example, other suitable subtraction structures may be applied to produce IHMT images. For example, an IHMT image may be produced after subtracting a dual frequency image, such as represented by imaging data set C from either a positive imaging data set, imaging data set A, and negative imaging data set, such as imaging data set B, which is termed "direct subtraction" and defined as follows $$IHMT_2 = A - C \quad (2);$$

$$IHMT_3 = B - C \quad (3).$$

In the methods of direct subtraction, small asymmetries of MT or field nonuniformities may causes errors. To this end, the application of equation 1 may give a first order correction for these errors.

As another example, two separate sets of dual frequency images, such as represented by imaging data set C may be acquired. To obtain an IHMT image having optimal signal-to-noise ratio, two separate sets of dual frequency images, acquired independently, may be preferable than the one multiplying a single dual frequency images by two.

In yet another example, simultaneous application of power at two frequencies may be applied to produce IHMT images. A method in accordance with the present disclosure can achieve this by sinusoidally modulating an RF pulse to produce power at both frequencies simultaneously. By using sinusoidally modulated pulses for simultaneous dual frequency modulation, a method in accordance with the present disclosure demonstrates significant advantages as the bandwidth of the pulse, defined by the envelope amplitude, may be made narrow while producing dual frequency modulation. Comparably, when pulses are used, they must be kept short, thus having high bandwidth. Further, the gap between positive and negative pulses in IHMT can be an important parameter affecting the signal of the resulting image.

The above-described techniques demonstrate that IHMT imaging can be used, for example, to target methylene (—CH$_2$—) chains in lipid bilayers as magnetization transfer agents. These protons only weakly interact with other protons due to the frequent bending of the methylene bonds, as described by Seiter and Chan in *H J Am Chem Soc* 95(23): 7541-53 1973 and by Chan, et al., in *Nature* 231:110-112 1971. However, to fully harness IHMT as a contrast mechanism, it is helpful to understand the underlying physical phenomenon. Thus, a series of experiments to further characterize the behavior of the IHMT signal were performed.

First, the timescale over which one could switch between positive and negative frequencies was investigated. While seeking to characterize this timescale, it was discovered that switching on a timescale longer than the spin diffusion time for protons in methylene chains caused a reduction in the signal. An example of the this time scale is 5 ms, which is in reasonable agreement with the expectations for diffusion times of methylene chains in lipid bilayers and has been estimated at around 8 ms by Feigenson and Chan, in *H J Am Chem Soc* 96(5):1312-9 1974. This estimate of exchange time was found to be highly insensitive to the assumed T2 of the protons.

For example, using a pulse sequence having a saturation scheme at a positive, negative, and combined offset frequency, in which the offset alternates between the two, the exchange time of the IHMT contrast mechanism could be determined. Using a 2 pool model for exchange in which irradiation at the positive offset is assumed to be disconnected from that at the negative offset, the IHMT effect could be modeled based on the assumption of saturation of a single line. The magnetization change following irradiation at the positive offset is given by:

$$\frac{\partial M_{ON}}{\partial t} = M_0 R_{ex} - M\left(R_{ex} + \frac{\omega_1^2 T_2}{1 + \Delta^2 T^2}\right); \quad (4)$$

whilst during periods of negative offset saturation the magnetization given by:

$$\frac{\partial M_{OFF}}{\partial t} = M_0 R_{ex} - M R_{ex}; \quad (5)$$

recovers on a timescale $R_{ex} = 1/\tau_{ex}$, assuming $R_{ex} \gg R_1$. In relation to an alternating frequency offset scheme associated with IHMT, the average magnetization, $M_{av}$, is thus given by the integral of $M_{ON}$ as:

$$M_{ON} = M_1 e^{-R'_{ex}t} + M_0(1 - e^{-R'_{ex}t}) \quad (6);$$

from t=0 to t=w and $M_{OFF}$ as:

$$M_{off} = (M_1 e^{-R'_{ex}w} + M'_0(1 - e^{-R'_{ex}w}))e^{-(t-w)R_{ex}} + M_0 \\ (1 - e^{-(1-w)R_1}) \quad (7);$$

from t=w to t=2w, divided by 2w, where $R'_{ex} = R_{ex} + \omega_1^2 T_2 / (1 + \Delta^2 T_2^2)$, $M'_0 = M_0 R_{ex}/R'_{ex}$, $M_1$ is the steady-state magnetization at t=w, where $M_{ON} = M_{OFF}$, and w is the saturation period. For sufficiently high RF power, this expression becomes independent of T2 and the dependence on w can be used to estimate Rex. (8);

Once Rex is estimated as above, T2 can be estimated from measuring IHMT at several different powers of applied RF.

The IHMT ratio (IHMTR) is calculated as $M_{ON}+M_{OFF}-2M_{av})/M_0$. Adopting a continuous wave (CW) scheme to investigate saturation the average magnetization, $M_{av}$ is now given by:

$$M_{av} = \frac{M_0 R_{ex}}{\left(R_{ex} + \frac{\frac{\omega_1^2}{2} T_2}{1+\Delta^2 T_2^2}\right)}; \quad (8)$$

so that IHMT equals $M_0 T_2^2 \omega_1^4 / ((R_{ex}+T_2\omega_1^2)(2R_{ex}+T_2\omega_1^2))$. With this information in hand, the exchange time, $\tau_{ex}$ and $T_2$ associated with an inhomogeneous component can be determined with IHMT. Furthermore, distinct values for exchange time correlate with clinical indications. As such, exchange time can be used as a mechanism to investigate clinical indications, including those that have and can be difficult to diagnose, such as traumatic injury and others. In such settings, a 3D pulse sequence, such as described below, may be advantageous.

Using an estimate of the exchange time, the T2 of the signal could be estimated because saturation depends on T2 and the exchange time. A pulse sequence with a short period of RF irradiation was used. To focus the bandwidth, a constant amplitude pulse for 50-100 ms was used and modulated sinusoidally to achieve dual frequency irradiation. By varying the pulse power, near saturation of the IHMT effect was achieved, thereby allowing for estimation of T2. T2s were measured in the 200 μs range, consistent with the expectations of prior studies of lipid membranes. Further, a spatial variation of the T2, which is attributable to errors resulting from B1 inhomogeneities, were present. Correction for these B1 inhomogeneities can be compensated for by using a B1 mapping sequence.

Though imaging of myelin provides a highly-valuable clinical use for the present invention, IHMT-based imaging serves as a general contrast mechanism that can be used for a variety of clinical and non-clinical imaging and analysis techniques. For example, the IHMT contrast mechanism can be used to analyze other substances that are not necessarily organic, such as a laminar liquid crystal of fatty alcohols. Fatty alcohols, having chains of methylene protons, are can be investigated using IHMT imaging. Quantification of exemplary fatty alcohols, such as hair conditioners, showed longer diffusion times, but shorter T2s than in-vivo white matter for samples. These observations also confirm the above-described IHMT contrast mechanism.

Figure 2:
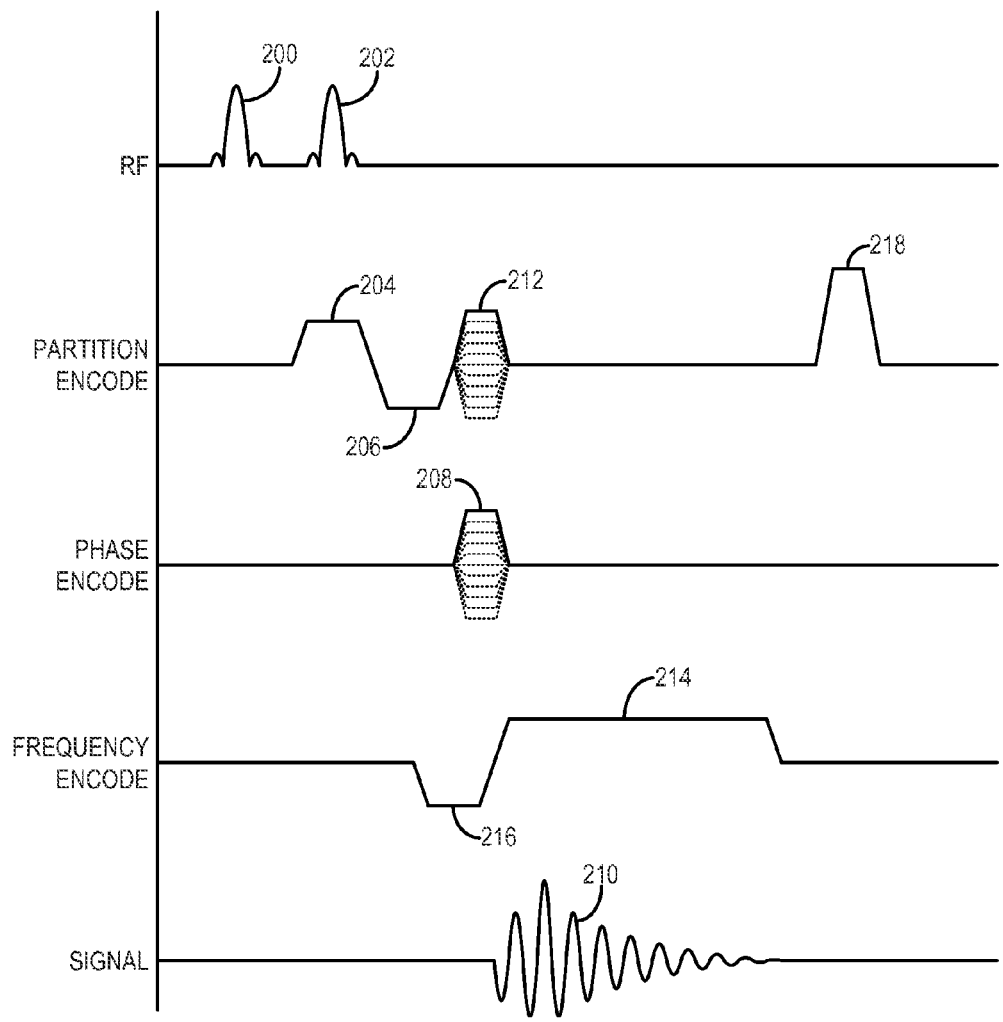
FIG. 2 is a pulse sequence diagram illustrating an example of a three-dimensional spoiled gradient-recalled echo pulse sequence having a magnetization transfer pulse module that can be employed when implementing the present invention.

Referring now to FIG. 2, an example of a pulse sequence that can be employed when practicing an IHMT technique in accordance with the present disclosure is illustrated. This pulse sequence is based on a spoiled gradient-echo ("SPGR") sequence with a MT module applied within each TR. In this non-limiting example, four experiments can be used to form the IHMT technique, each with a different saturation module. Of course, other numbers of experiments/acquisitions may be performed. In this example, in the first and third case, a trapezoidal pulse of duration 5 ms and B1,peak=50 mG can be independently applied at offsets of +5 kHz (P) and −5 kHz (N) prior to the SPGR. In the second and fourth, a cosine-modulated trapezoidal pulse can be employed with B1,peak=(√2)50 mG on-resonance (D). An IHMT image, and consequent ratio image (IHMTR), can then be formed by P+N−2D divided by an unsaturated acquisition.

The pulse sequence begins with the application of a saturation radio frequency ("RF") pulse 200. Preferably, the RF pulse is a simple shape that is sinusoidally modulated to achieve dual frequency irradiation; however, a composite pulse consisting of multiple shorter pulses with frequency alternating between pulses for dual frequency saturation can also be applied. The saturation pulse 200 is applied at a selected off-resonance frequency in order to saturate some of the exchangeable magnetization of bound pool spins. As discussed above, the frequency of the RF pulses is changed depending on the type of image to be obtained. By way of example the RF pulse 200 may include an amplitude-modulated RF pulse that is capable of saturating spins at two frequencies simultaneously. As described above, one example of such a pulse is a sinusoidally-modulated pulse. Following the application of the saturation pulse 200, data acquisition occurs.

The example SPGR pulse sequence includes a spatially selective RF excitation pulse 202 that is repeated at the start of each repetition time ("TR") period. Moreover, the RF excitation pulse 202 is played out in the presence of a slice-selective gradient 204 in order to produce transverse magnetization in a prescribed imaging slice. The slice selective gradient 204 includes a rephasing lobe 206 that acts to rephase unwanted phase accruals caused by the RF excitation pulse 202. Following excitation of the nuclear spins in the prescribed imaging slice, a phase-encoding gradient 208 is applied to spatially encode a nuclear magnetic resonance signal, representative of a gradient-recalled echo 210, along one direction in the prescribed imaging slice. To enable three-dimensional imaging, a partition-encoding gradient 212 is applied concurrently with the phase-encoding gradient 208 to spatially encode the magnetic resonance signal along a second orthogonal direction. A readout gradient 214 is also applied after a dephasing gradient lobe 216 to spatially encode the signal representative of the echo 210 along a third, orthogonal direction in the prescribed imaging slice. The signal representative of the echo 210 is sampled during a data acquisition window. The pulse sequence concludes with the application of a spoiler gradient 218 that spoils the remaining transverse magnetization. Of course, the above-described SPGR pulse sequence is but one pulse sequence that can be used to elicit data using the IHMT contrast mechanism. Further more, the pulse sequence may be 2D or 3D.

Figure 3:
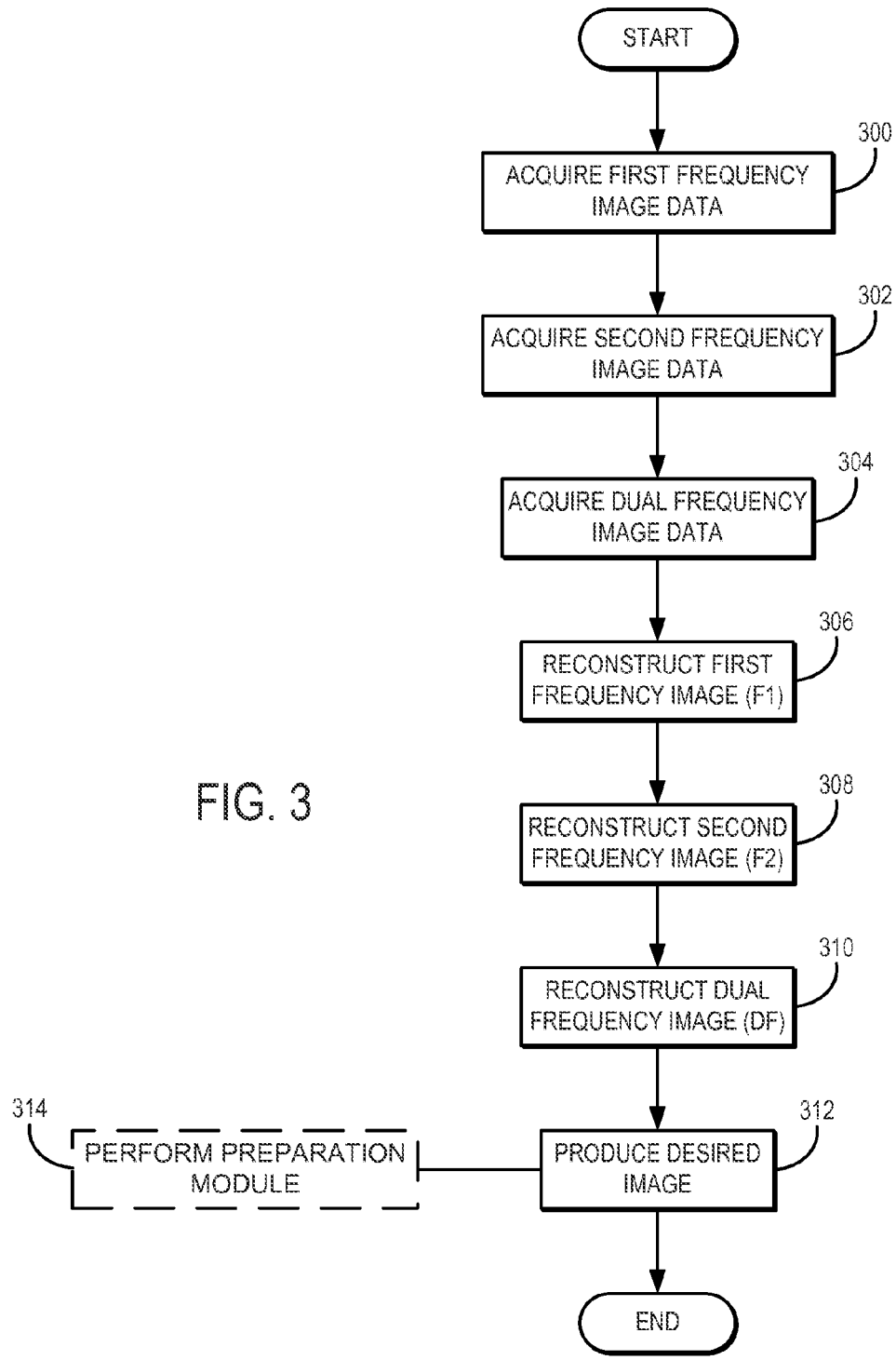
FIG. 3 is a flowchart setting forth the steps of an exemplary method for performing IHMT imaging in accordance with the present invention.

Referring now to FIG. 3, a flowchart setting forth the steps of an exemplary method for myelin specific imaging using inhomogeneous magnetization transfer (IHMT) MRI techniques is illustrated. The method begins with the acquisition of three sets of image data. The first set of image data is acquired, as indicated at step 300, using a pulse sequence that applies RF saturation energy at a first frequency; thus, this first set of image data can be referred to as first frequency image data. By way of example, the pulse sequence illustrated in FIG. 2 can be used to acquire the first frequency image data. For the first frequency image data, the frequency of each RF pulse, or the continuous RF wave, is set to the first frequency, which can be selected such that some exchangeable magnetization of bound pool spins is saturated without directly saturating free water protons. For example, the first frequency can be selected as a frequency between 0.5 and 20 kHz.

Likewise, the second set of image data is acquired, as indicated at step 302, using a pulse sequence that applies RF saturation energy at a second frequency that is different than the first frequency; thus, this second set of image data can be referred to as second frequency image data. By way of example, the pulse sequence illustrated in FIG. 2 can also be used to acquire the second frequency image data. For the second frequency image data set, the frequency of each RF pulse, or the continuous RF wave, is set to the second frequency. For example, the second frequency can be selected as the negative of the first frequency. In one specific aspect of the present invention, the first and second frequencies are selected such that they are offset sufficiently far from the free water frequency to avoid saturating free water, but sufficiently close to protons of the methylene (—$CH_2$—) chains in lipid bilayers in myelin such that some of the magnetization in protons of those methylene chains is saturated.

The third set of image data, referred to as the "dual frequency," is acquired, for example, using the pulse sequence illustrated in FIG. 2 as indicated at step 304. For the dual frequency image data, the frequency of the RF pulses alternate between the first and second frequencies employed in steps 300 and 302. For example, the frequency of the odd-numbered RF pulses is selected as the first frequency, whereas the frequency of the even-numbered RF pulses is selected as the second frequency. In the alternative, however, each RF pulse may include two frequency bands: one centered about the first frequency and one centered about the second frequency. By way of example, continuous RF wave saturation at both the reference and labeling frequency can be achieved using amplitude modulation of the continuous RF wave, such as by:

$$B_1(t) = \sqrt{2} \cdot B_1 \sin(\omega t) \quad (9);$$

where $B_1(t)$ is the continuous RF wave; $B_1$ is the amplitude of the continuous RF wave; $\omega$ is the first frequency, for which $-\omega$ is the second frequency; and t is time. This amplitude modulation generates a frequency response with components at both $+\omega$ and $-\omega$.

After the three image data sets described above are acquired, images are reconstructed from the respective data sets. As indicated at step 306, a first frequency ("F1") image is reconstructed from the first frequency image data. This image reconstruction is a conventional image reconstruction process; however, it will be appreciated by those skilled in the art that any number of image reconstruction methods can be employed without detracting from the present invention. Similarly a second frequency ("F2") image is reconstructed from the second frequency image data, as indicated at step 308. Lastly, a dual frequency ("DF"), or an IHMT, image is reconstructed from the dual frequency, image data, as indicated at step 310. An image depicting substantially only the desired exchangeable magnetization from the inhomogeneously broadened bound pool protons is produced by selectively combining the F1, F2, and DF images, as indicated at step 312. For example, the image may be a difference image produced in accordance with equation 1. It will be appreciated by those skilled in the art that subtraction of image data prior to image reconstruction, and subsequently reconstructing a single image from such difference data, would be functionally equivalent to subtracting the respective images after reconstruction.

In addition to acquiring three image data sets as described above, in some instances it may be advantageous to acquire a second dual frequency image data set, thereby acquiring four total image data sets. Also, other numbers of data sets are contemplated. By way of example, when pulsed RF energy is used it may be beneficial to acquire a first dual frequency image data set by alternating the frequency of the RF pulses between the first frequency (odd pulses) and the second frequency (even pulses). A second dual frequency image data set may then be acquired by alternating the frequency of the RF pulses between the first frequency (even pulses) and the second frequency (odd pulses). A first and second dual frequency image may then be reconstructed from these first and second dual frequency image data sets, respectively. The first and second dual frequency images may then be averaged together to obtain an average dual frequency image that is selectively combined with the labeled and reference images. Also, as will be described, a preparation module at step 314 may optionally be used to create the reference image. To this end, the optional preparation module at step 314 may precede the acquisition of the first frequency image data at step 300 or at other suitable positions in the above-described process.

When the RF pulses are alternated between the first and second frequencies, the last RF pulse has to be one or the other. The slight timing difference between the last first frequency pulse and the last second frequency pulse will result in a small, systematic error. Thus, by switching the manner in which the pulses are alternated between the first and second frequencies, and then averaging the two resultant dual frequency images, these small, systematic errors may be mitigated.

The herein described IHMT method for magnetic resonance imaging may provide for the imaging of exchangeable magnetization of bound pool protons that is much more robust to variations in the water frequency caused by non-uniform magnetic fields than prior single reference techniques. However, in some applications, additional correction of water frequency offset effects may be desirable. In these instances, the IHMT method may be repeated with a different frequency offset being added to the first and second frequencies during each repetition. For example, a frequency offset of +0.5 ppm may be applied to both the first and second frequencies during a given repetition. By varying the frequency offset during each repetition, multiple first, second, and dual frequency image data sets may be obtained, from which a set of multiple first, second, and dual frequency images may be reconstructed. The information contained in these images can be used to correct for water frequency offsets by, for example, interpolating the information contained in each set of the reconstructed images to a larger set of data points and shifting the resulting interpolated data using a fitted z-spectrum water frequency offset for each voxel location in the images. These shifted first, second, and dual frequency images that were acquired using the non-offset first and second frequencies are then selectively combined as described above to arrive at the desired images.

Similar to the technique described, the herein described IHMT method can be repeated with a different frequency offset being added to the first and second frequencies during each repetition to acquire sets of multiple first, second, and dual frequency images. In this instance, however, the sign of the frequency offset as applied to the first frequency is changed before applying to the second frequency. For example, if a frequency offset of +0.5 ppm is applied to the first frequency, then a frequency offset of −0.5 ppm is applied to the second frequency. Using the sets of multiple images acquired in this manner, the frequency spectrum of the exchangeable magnetization of bound pool protons can be determined. Such a spectrum may contain information about the center frequency of the protons, which may vary with different biochemical contents, and also about the T2 relaxation of the protons. The frequency spectrum can also provide information about the chemical structures containing the inhomogeneously broadened protons, and may assist quantification of exchange rate and quantification.

The herein described IHMT acquisition may also be repeated using different RF power levels during each repetition. By way of example, the different power level may be achieved by changing the pulse repetition rate or pulse amplitude when pulsed RF energy is used, or by changing the amplitude of the continuous wave RF energy when continuous wave RF energy is used. By varying the power level in subsequent acquisitions, images with different sensitivity to proton exchange rate and exchangeable magnetization concentration are obtained. The exchange rate and exchangeable magnetization concentration measurable with the present invention reflect inhomogeneous magnetization transfer from a broad line. The images may also be subtracted or otherwise mathematically combined to produce images indicative of either exchangeable magnetization concentration or exchange rate without the need to calculate measured values.

As described above, the herein-described IHMT acquisition shows the corresponding IHMT signal and the as-measured T2 sensitive to errors in power from miscalibration or non-uniformity. However, as the power is increased, the IHMT effect begins to saturate and the signal becomes much less sensitive to the power amplitude. Because the RF power can vary across the sample or tissue of interest because of RF coil geometry or electrical properties of tissue, reduced sensitivity to power amplitude is desirable. Reduced power sensitivity images will be more reflective of tissue properties and less reflective of equipment and calibration effect. Higher power saturation may not be possible for long durations because of safety limits on RF power deposited in patients or hardware limits on the average power of RF systems. Applying a shorter, high power preparation pulse sequence that achieves approximate saturation of the IHMT effect may achieve the RF power insensitivity while remaining within the safety and equipment requirements. Because IHMT tends to increase proportional to power until near saturation, applying higher RF power for shorter duration but achieving comparable average RF power to a longer application of RF at lower power should provide a similar level of IHMT effect. Thus, a power-insensitive IHMT imaging may be achieved using high power and a short duration. Such a power-insensitive IHMT imaging will be more reflective of myelin differences across the brain.

As described above, a system and method is provided to generate measurements, or images, that isolate the effect of magnetization transfer of a particular targeted pool from the effects of other pools, tissue properties, or properties of the measurement device. This is particularly useful for the measurement of more subtle effects, such as chemical exchange saturation transfer or IHMT in the presence of the larger effects of magnetization transfer from broad macromolecules and tissue relaxation. Successful isolation of particular exchange effects can increase tissue contrast, quantitative accuracy, and potentially diagnostic accuracy of imaging.

Typically, the ratio of the signal difference between two experiments to the unsaturated image (i.e. MTR) is used as a measure of the MT effect. However, the present disclosure recognizes that this is an imperfect measure because it mixes together direct saturation effects and different MT components in a nonlinear way. Though such data can be fit to a complex model, a simple analytic quantification with a minimal number of points is more desirable. Thus, in accordance with the present disclosure, an alternative formulation may be used to facilitate quantification of MT phenomena.

More particularly, as explained above, MT may involve one or more pools in exchange with the visible, free pool. As long as the RF is not sufficiently powerful and on-resonance to rotate the transverse magnetization beyond a small angle from the z-direction, the Bloch equations for each MT component can be reduced to:

$$\frac{\delta M_B}{\delta t} = (M_B^0 - M_B)R_B - R(M_A^0 M_B - M_B^0 M_A) - R_B^{rf} M_B;$$ Eqn. (10)

where, following the notation of Henkelman et al. (Magnetic Resonance in Medicine 29:759-766 1993), B is the bound pool, A is the visible pool, and the saturation effect of RF power is given by:

$$R_B^{rf} = \omega_1^2 \pi g_B(2\pi\Delta)$$ Eqn. (11);

with g a function, such as Lorentzian, Gaussian or Super Lorentzian. For example, Lorentzian being:

$$R_B^{rf} = \frac{\omega_1^2 T_2}{1 + (2\pi\Delta T_2)^2};$$ Eqn. (12)

with T2 potentially affected by the exchange rate. If a steady state is assumed and it is assumed that exchange and saturation dominate relaxation, such that $(R_B^{rf} + RM_A^0) \gg R_B$, then a simple steady state occurs, such that:

$$M_B = \frac{RM_B^0 M_A}{RM_A^0 + R_B^{rf}}.$$ Eqn. (13)

Assuming many such components and substituting in the equation for the steady state visible magnetization gives:

$$M_A = \frac{M_A^0 R_A}{\left(R_A + RM_B^0 + R_A^{rf} - \frac{RM_B^0}{1 + \frac{R_B^{rf}}{M_A^0 R}}\right)} = \frac{M_A^0 R_A}{\left(R_A + R_A^{rf} + \frac{R_B^{rf} RM_B^0}{M_A^0 R + R_B^{rf}}\right)}.$$ Eqn. (14)

Note, if there are more than one MT components (MB) but they all meet the criterion for exchange dominance, they add to provide:

$$M_A = \frac{M_A^0 R_A}{\left(R_A + R_A^{rf} + \sum_i \frac{R_i^{rf} R_{Ai} M_i^0}{M_A^0 R_{Ai} + R_i^{rf}}\right)};$$ Eqn. (15)

individual exchange rates are defined Ai.

Examples of multiple components may include Chemical Exchange Saturation Transfer (CEST) (Ward et al. Journal of Magnetic Resonance. 2000 143:79-87.) or IHMT. If the conventional MT ratio is used the equation takes the form:

$$MTR = 1 - \frac{M_A}{M_A^0} = \frac{R_A^{rf} + \sum_i \frac{R_i^{rf} R_{Ai} M_i^0}{M_A^0 R_{Ai} + R_i^{rf}}}{\left(R_A + R_A^{rf} + \sum_i \frac{R_i^{rf} R_{Ai} M_i^0}{M_A^0 R_{Ai} + R_i^{rf}}\right)}; \qquad \text{Eqn. (16)}$$

And the result mixes all components together in nonlinear fashion. However, if the alternate expression is used the equation takes the form:

$$R1\,ratio = \frac{M_A^0}{M_A} - 1 = \frac{R_A^{rf} + \sum_i \frac{R_i^{rf} R_{Ai} M_i^0}{M_A^0 R_{Ai} + R_i^{rf}}}{R_A}; \qquad \text{Eqn. (17)}$$

and then the expression is linear in the exchange components. Differences between two experiments where one component of MT (and direct saturation) is fixed, such as positive vs. dual frequency in an IHMT experiment or positive and negative frequency in a CEST experiment where conventional MT is relatively unchanged, will become insensitive to the unchanging components. Only the original R1 is needed for quantification.

To a large extent, the steady state approach to MT with a low flip angle gradient echo imaging sequence and RF saturation pulses before each excitation, can be approximated as a steady state with a different R1 and M0 then equilibrium. The signal from a steady state sequence is given by:

$$S = M_0 \frac{\sin\alpha (1 - e^{-R_1 T_r})}{(1 - \cos\alpha \, e^{-R_1 T_r})}. \qquad \text{Eqn. (18)}$$

For R1 TR<<1 and α<<1, this becomes:

$$S = M_0 \frac{\alpha R_1 T_r}{\left(R_1 T_r + \frac{\alpha^2}{2}\right)}. \qquad \text{Eqn. (19)}$$

If power is applied, the M and R1 change gives:

$$M_0^* = \frac{M_0 R_1}{R_1^*}; \qquad \text{Eqn. (20)}$$

$$S^* = M_0 R_1 T_r \frac{\alpha}{\left(R_1^* T_r + \frac{\alpha^2}{2}\right)}. \qquad \text{Eqn. (21)}$$

Note that calculating MT differences using the inverse of S preserves the linearity in R1 that is an advantage of the true steady state:

$$S\Delta\left(\frac{1}{S^*}\right) = \frac{\Delta(R_1^*) T_r}{\left(R_1 T_r + \frac{\alpha^2}{2}\right)}. \qquad \text{Eqn. (22)}$$

This expression does produce a flip angle dependent result, however. There are two sources of RF field (B1) sensitivity, however, to this expression. The flip angle and the difference in R1. For many situations, the change in R1 dependence is proportional to power. In this case, a reference image can be acquired with the flip angle increased by a factor of C, such that the right, flip angle dependent term in the denominator is much larger than the term on the right:

$$\frac{S_C}{C} \Delta\left(\frac{1}{S^*}\right) = \frac{\Delta(R_1^*) T_r}{\left(R_1 T_r + \frac{C^2 \alpha^2}{2}\right)}. \qquad \text{Eqn. (23)}$$

A factor of 2 or 3 should largely remove all B1 sensitivity. This has the other advantage that the result becomes independent of R1. On the other hand, if the change in R1 is saturated (i.e. independent of B1) as can occur for a slowly exchanging CEST line on resonance, then C should be set substantially less than one.

While this strategy naturally suggests itself for steady state gradient echo sequences, the same approach can be used for a long, steady state preparation of a fast readout sequence, such as EPI or RARE. In this case, the readout is eliminated but the option for a low flip angle, RF spoiled RF pulse on resonance is preserved. The sin alpha term now vanishes. We can therefore use a zero flip for the MT preparation sequences. For the reference image, a nonzero flip angle such that 1-cos(alpha) is much greater that R1Tr is used.

Thus, as described above, in the steady state, linearity can be achieved by subtracting the inverse of the magnetization measured under different irradiation. This is particularly useful for studies of more subtle differences in magnetization after irradiation with different powers or frequency distributions, as is used for CEST or for multi-frequency irradiation, such as described above.

That is, as explained, measurement of magnetization transfer includes the comparison of two or more images with different off-resonance irradiation. Conventionally this comparison is performed by subtraction of images. The problem with this approach is that images acquired with saturation are not linearly dependent on magnetization transfer. This nonlinearity mixes together magnetization transfer effects with direct saturation and relaxation effects. It is even more of a problem when trying to identify a smaller component of MT (such as inhomogeneous MT or CEST) in the presence of a larger, undesired MT contribution. If subtraction is used, the more subtle effect of IHMT or CEST will be modulated by the undesired MT contribution.

As described above, subtracting the inverse of the signals from images acquired with different off-resonance saturation provides almost complete separation of the desired MT components from other MT components. In the case of IHMT, one can calculate:

$$IHMTR_1 = S_{ref}\left(\frac{2}{S_{dual}} - \frac{1}{S_{pos}} - \frac{1}{S_{neg}}\right); \qquad \text{Eqn. (24)}$$

where the subscripts are "pos" for positive offset single frequency saturation, "neg" for negative offset single frequency saturation, "dual" for dual frequency saturation, and "ref" for a reference image, typically one without any off-resonance saturation. This provides separation of the IHMT effect from other MT components whereas the more traditional relationship, $$IHMTR = \left(\frac{S_{pos} + S_{neg} - 2S_{dual}}{S_{ref}}\right),$$

provides a measure that, while still zero if there is no IHMT, it is nonlinearly dependent on other parameters, especially conventional broad macromolecular MT. However, as shown above, for steady state gradient echo pulsed MT, this inverse subtraction is similarly desirable for steady state gradient echo pulse sequences.

Even with the separation of the desired MT component from other MT components by inverse subtraction, the measured MT component is dependent upon the relaxation rate in the tissue (referred to as R1 or 1/T1) and any errors in the applied off-resonance RF magnetic field. These can occur either because the RF is miscalibrated or because the distribution of RF field is spatially nonuniform, because of imperfections in the hardware used to created the RF field (typically referred to as an RF coil) and/or because the dielectric properties of tissue distort the RF field.

In a steady state gradient echo MT experiment using inverse subtraction such as described above, choosing a higher flip angle for the reference image (for example 40 degrees instead of the 10 degrees used for the MT image acquisition) created an image that became independent of R1 and the applied RF magnetic field strength. An extension of this approach could also be used if a prepared sequence is instead employed. In preparation, the RF can be applied to create a certain magnetization and then the image is rapidly sampled in a way that the image intensity is proportional the magnetization just before the image acquisition. An appropriate T1 weighted reference image can be created by applying repeated RF pulses on resonance, just like the excitation pulses of a steady state gradient echo sequence.

Thus, the above-described approach recognizes that, when low flip angle steady state sequences are employed, the RF field and tissue T1 sensitivity of the measurement can be greatly reduced by acquiring a reference image, without RF, at a different flip angle. For magnetization transfer saturation that is dependent upon power, as occurs in transfer from broad lines, from inhomogeneous lines or from sufficiently rapidly exchanging CEST lines, the use of a reference image with substantially larger flip angle can substantially eliminate RF and T1 dependence of the measurement.

The above-described approach further recognizes that the benefits of RF field and tissue T1 insensitivity can also be obtained when using RF irradiation as a prepared sequence. A preparation of off-resonance saturation pulses and weaker on resonance, spoiled RF pulses, but without imaging readout, will achieve the same effect as a preparation for a readout sequence such as EPI, RARE, or other such sequences. In fact, the flip angle during the MT preparation can be set to zero and then increased to a larger value, 30-40 degrees, for the reference scan.

With the inverse subtraction and T1 weighted reference image an approach is provided to measure IHMT, CEST, or conventional MT without sensitivity to other parameters of tissue or properties of the imaging system. This is a greatly improved approach to quantifying these parameters that removes a major obstacle to fast and reproducible imaging and measurement of such properties. Thus, the above-described techniques can be used to quantify magnetization transfer, even from otherwise difficult to image or measure molecules that exchange with more freely moving water. Such measurements can be used in a variety of clinically useful situations. For example, such techniques may be used to provide measurements related to myelin, pH, glucose concentration, and other physiologically relevant quantities. For all these studies, the effects of transfer from the target molecules, other magnetization transfer, T1 of tissue combines together in a nonlinear fashion that makes quantification of the target molecules challenging and the present techniques overcome this challenge. In addition, such measurements are highly sensitive to the calibration and uniformity of the applied RF irradiation and the present techniques overcome these challenges. That is, the present disclosure has provided systems and methods for separating the magnetization transfer components and controlling the T1 and RF sensitivity of the measurement. This strategy improves reproducibility across sites, field strengths, and vendor platforms, and enables improved diagnosis and clinical evaluation of myelination, pH, and other important physiologic quantities.

Figure 4:
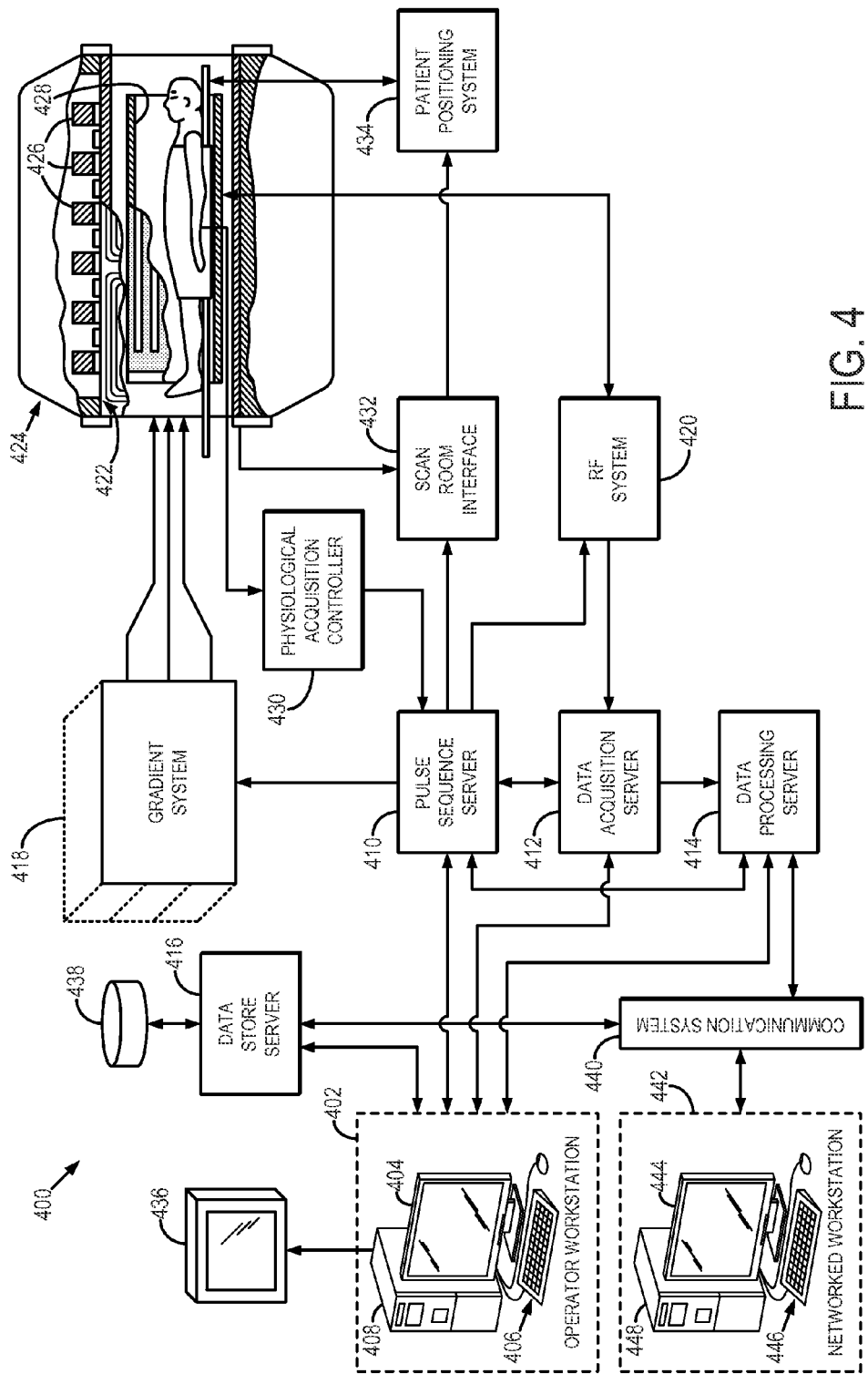
FIG. 4 is a block diagram of an exemplary magnetic resonance imaging ("MRI") system that employs the present invention.

Referring particularly now to FIG. 4, an example of a magnetic resonance imaging ("MRI") system 400 that may be used to implement the present invention is illustrated. The MRI system 400 includes a workstation 402 having a display 404 and a keyboard 406. The workstation 402 includes a processor 408, such as a commercially available programmable machine running a commercially available operating system. The workstation 402 provides the operator interface that enables scan prescriptions to be entered into the MRI system 400. The workstation 402 is coupled to four servers: a pulse sequence server 410; a data acquisition server 412; a data processing server 414; and a data store server 416. The workstation 402 and each server 410, 412, 414, and 416 are connected to communicate with each other.

The pulse sequence server 410 functions in response to instructions downloaded from the workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding MR signals. The gradient coil assembly 422 forms part of a magnet assembly 424 that includes a polarizing magnet 426 and a whole-body RF coil 428.

RF excitation waveforms are applied to the RF coil 428, or a separate local coil (not shown in FIG. 4), by the RF system 420 to perform the prescribed magnetic resonance pulse sequence. Responsive MR signals detected by the RF coil 428, or a separate local coil (not shown in FIG. 4), are received by the RF system 420, amplified, demodulated, filtered, and digitized under direction of commands produced by the pulse sequence server 410. The RF system 420 includes an RF transmitter for producing a wide variety of RF pulses used in MR pulse sequences. The RF transmitter is responsive to the scan prescription and direction from the pulse sequence server 410 to produce RF pulses of the desired frequency, phase, and pulse amplitude waveform. The generated RF pulses may be applied to the whole body RF coil 428 or to one or more local coils or coil arrays (not shown in FIG. 4).

The RF system 420 also includes one or more RF receiver channels. Each RF receiver channel includes an RF preamplifier that amplifies the MR signal received by the coil 428 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad (25);$$

and the phase of the received MR signal may also be determined:

$$\varphi = \tan^{-1}\left(\frac{Q}{I}\right). \quad (26)$$

The pulse sequence server 410 also optionally receives patient data from a physiological acquisition controller 430. The controller 430 receives signals from a number of different sensors connected to the patient, such as electrocardiograph ("ECG") signals from electrodes, or respiratory signals from a bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized MR signal samples produced by the RF system 420 are received by the data acquisition server 412. The data acquisition server 412 operates in response to instructions downloaded from the workstation 402 to receive the real-time MR data and provide buffer storage, such that no data is lost by data overrun. In some scans, the data acquisition server 412 does little more than pass the acquired MR data to the data processor server 414. However, in scans that require information derived from acquired MR data to control the further performance of the scan, the data acquisition server 412 is programmed to produce such information and convey it to the pulse sequence server 410. For example, during prescans, MR data is acquired and used to calibrate the pulse sequence performed by the pulse sequence server 410. Also, navigator signals may be acquired during a scan and used to adjust the operating parameters of the RF system 420 or the gradient system 418, or to control the view order in which k-space is sampled. In all these examples, the data acquisition server 412 acquires MR data and processes it in real-time to produce information that is used to control the scan.

The data processing server 414 receives MR data from the data acquisition server 412 and processes it in accordance with instructions downloaded from the workstation 402. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 414 are conveyed back to the workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the workstation 402. The workstation 402 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

We claim:

1. A method for producing a report about a subject from data collected from the subject using a magnetic resonance imaging (MRI) system, the steps of the method comprising:
    a) directing the MRI system to perform at least one pulse sequence that includes applying radio frequency (RF) energy at least at two frequencies, wherein the RF energy is suitable to manipulate magnetization that is transferred from protons in the subject that are bound to macromolecules to free water protons;
    b) acquiring, with the MRI system, imaging data including magnetization transfer information from the magnetization from protons in the subject that are bound to macromolecules;
    c) based on the imaging data acquired in step b), producing images indicative of an exchange time of the magnetization from protons in the subject that are bound to macromolecules, wherein the exchange time is reflective of motion restriction or spin diffusion of the protons bound to macromolecules.

2. The method as recited in claim 1 which further includes using the exchangeable time as a contrast mechanism to indicate a clinical condition.

3. The method as recited in claim 1 in which step a) includes applying multiple RF pulses at one of a first frequency and a second frequency that is different from the first frequency using an amplitude modulated RF pulse.

4. The method as recited in claim 3 in which the RF pulses applied at the first frequency and the RF pulses applied at the second frequency are applied simultaneously.

5. The method as recited in claim 1 in which step a) includes applying RF pulses at both a first frequency and a second frequency that is different than the first frequency using a sinusoidally modulated RF pulse that produces power at both the first frequency and the second frequency.

6. The method as recited in claim 5 in which the RF pulses applied at the first frequency and the RF energy applied at the second frequency are applied simultaneously.

7. The method as recited in claim 1 in which step a) includes applying multiple RF pulses having a duration of time separating the multiple RF pulses.

8. The method as recited in claim 7 in which the duration of time separating the multiple RF pulses is longer than the spin diffusion time for protons bound to macromolecules.

9. The method as recited in claim 8 in which the duration of time separating the multiple RF pulses is about five milliseconds.

10. The method as recited in claim 7 in which step c) includes determining the exchange time.

11. The method as recited in claim 10 which determining the exchange time is based on the dependence of the transferred magnetization and the corresponding magnetic resonance signals on the saturation period (w) corresponding to the duration of time separating the multiple RF pulses.

12. The method as recited in claim 1 in which step c) comprises producing a map that depicts an exchange time of the transferred magnetization.

13. The method as recited in claim 12 further comprising producing a map that depicts transverse relaxation time using the produced map that depicts the exchange time of the magnetization.

14. The method as recited in claim 1 further comprising:
performing, with the MRI system, a preparation module to acquire reference data using a predetermined flip angle;
reconstructing the reference image from the reference data; and
using the reference image to control R1 and RF power (B1) errors.

15. The method as recited in claim 14 in which step b) includes acquiring first frequency image data associated with applying the RF energy at a first frequency and dual frequency image data associated with applying the RF energy at the first frequency and a second frequency and wherein step c) includes determining signal difference in the first frequency image data and the dual frequency image data acquired in step b).

16. The method as recited in claim 15 in which step b) includes acquiring second frequency image data associated with applying the RF energy at the second frequency and in which step c) includes determining signal differences in the first frequency image data, the second frequency image data, and the dual frequency image data acquired in step b).

17. The method as recited in claim 1 in which step c) includes performing a subtraction of an inverse of the signal to separate magnetization transfer components of the transferred magnetization of protons in the subject.

18. The method as recited in claim 1 in which a transverse relaxation time (T2) is estimated by performing the measurement at several different powers of applied radiofrequency irradiation.

* * * * *

UNITED STATES PATENT AND TRADEMARK OFFICE
CERTIFICATE OF CORRECTION

PATENT NO. : 10,302,722 B2  
APPLICATION NO. : 14/776872  
DATED : May 28, 2019  
INVENTOR(S) : David Alsop et al.

Page 1 of 1

It is certified that error appears in the above-identified patent and that said Letters Patent is hereby corrected as shown below:

In the Specification

Column 6, Line 55, Eq. (6), "$M_{ON} = M_1 e^{-R_{ex}^1 t} + M_0 (1 - e^{-R_{ex}^1 t}}$" should be $$M_{ON} = M_1 e^{-R_{ex}^1 t} + M_0 \left(1 - e^{-R_{ex}^1 t}\right)$$ --.

Column 6, Line 58, Eq. (7),

"$M_{off} = \left( M_1 e^{-R_{ex}^1 w} + M_0' \left(1 - e^{-R_{ex}' w}\right) \right) e^{-(t-w)R_{ex}} + M_0 \left(1 - e^{-(1-w)R_1}\right)$" should be $$M_{OFF} = \left( M_1 e^{-R_{ex}^1 w} + M_0' \left(1 - e^{-R_{ex}' w}\right) \right) e^{-(t-w)R_{ex}} + M_0 \left(1 - e^{-(1-w)R_1}\right)$$ --.

Signed and Sealed this  
Tenth Day of September, 2019

Andrei Iancu  
*Director of the United States Patent and Trademark Office*